United States Patent [19]

Bosche et al.

[11] Patent Number: 4,490,214

[45] Date of Patent: Dec. 25, 1984

[54] PROCESS FOR THE PREPARATION OF STORAGE-STABLE ALKYLENE GLYCOL MONOALKYL ETHERS

[75] Inventors: Horst G. Bosche, Speyer; Heinz Nohe, Meckenheim; Heinz Pachaly, Limburgerhof, all of Fed. Rep. of Germany

[73] Assignee: BASF Aktiengesellschaft, Ludwigshafen, Fed. Rep. of Germany

[21] Appl. No.: 392,088

[22] Filed: Jun. 25, 1982

[30] Foreign Application Priority Data

Jun. 26, 1981 [DE] Fed. Rep. of Germany ....... 3125107

[51] Int. Cl.$^3$ .......................... B01D 3/34; C07C 41/42
[52] U.S. Cl. .......................................... 203/6; 203/29; 568/618; 568/621
[58] Field of Search .................. 203/6, 29, 38, 50, 49; 568/621, 618, 622

[56] References Cited

U.S. PATENT DOCUMENTS

| | | | |
|---|---|---|---|
| 2,922,831 | 1/1960 | Bloch et al. | 203/6 |
| 2,983,763 | 5/1961 | Krause | 568/621 |
| 3,410,760 | 11/1968 | Craig et al. | 203/14 |
| 3,991,122 | 11/1976 | Gritti | 568/618 |

FOREIGN PATENT DOCUMENTS

| | | | |
|---|---|---|---|
| 52-3923 | 1/1977 | Japan | 568/618 |
| 55-89236 | 7/1980 | Japan | 568/621 |
| 7317387 | 6/1974 | Netherlands | 568/618 |

Primary Examiner—Wilbur Bascomb
Attorney, Agent, or Firm—Joseph D. Michaels; David L. Hedden

[57] ABSTRACT

The subject invention relates to the preparation of storage-stable alkylene glycol monoalkyl ethers having the general formula $$R\text{—}(O\text{—}A\text{—})_n OH$$

in which A represents an ethylene or propylene group, R denotes a $C_1$–$C_4$-alkyl group, and n has a value of 1 to 4. They are prepared by carrying out the fractional distillation of a mixture which is produced by the alkali catalyzed reaction of ethylene oxide or propylene oxide with an alcohol in the presence of 0.1 to 20 ppm of ammonia based on the amount of the mixture.

5 Claims, No Drawings

PROCESS FOR THE PREPARATION OF STORAGE-STABLE ALKYLENE GLYCOL MONOALKYL ETHERS

This invention relates to a process for the preparation of storage-stable alkylene glycol monoalkyl ethers having the general formula $$R-(O-A-)_n OH \qquad (I)$$

in which A denotes an ethylene or propylene group, R represents a $C_1-C_4$-alkyl group, and n has a value of 1 to 4.

The ethers of propylene glycol and particularly of ethylene glycol are primarily used as water-soluble solvents in the coatings industry and furthermore represent important intermediates for organic syntheses.

On the other hand, corresponding ethers with two or more (—O —A—) units in the molecule, which are commonly, if not quite correctly, referred to as dialkylene glycol ethers, trialkylene glycol ethers and generally as polyalkylene glycol ethers, primarily serve as hydraulic fluids.

Compounds according to formula (I) are predominantly prepared in such a manner that ethylene oxide or propylene oxide are reacted with an alcohol (R-OH) in the presence of an acid or particularly a mineral base at temperatures of 100° C. to 220° C. and pressures of 2 bars to 50 bars resulting in mixtures of monoethers of alkylene glycol (n=1) and higher alkylene glycols (n=2 to 4) with different compositions depending upon the quantity ratios and the reaction conditions. As a rule, the excess alcohol is subsequently removed from these mixtures by distillation whereupon they are separated into their components by means of fractional distillation.

It has now been found that the fractions obtained in this manner are not storage-stable. For reasons which are not exactly known, acids form in the course of time which cause discolorations thereby considerably reducing the sales and usage value of products having formula I.

Therefore, the purpose of this invention was to stabilize the alkylene glycol monoalkyl ethers against the formation of acids during storage.

It was found that the alkylene glycol monoalkyl ethers, as defined above, remain stable against the formation of acid if the fractional distillation of the mixtures produced by the alkali catalyzed reaction of ethylene oxide or propylene oxide with the alcohol is carried out in the presence of 0.1 to 20 ppm of ammonia based on the amount of mixture used.

The effect of the ammonia in this case is not for the neutralization of the resultant acid. The quantities are much too low, especially since the ammonia is frequently hardly detectable in the distillate. In addition to this, the stabilizing effect remains comparatively low if the products according to formula I are mixed with the ammonia after the distillation. It must, therefore, be assumed that traces of interferring substances, which otherwise are allowed to enter the distillate where they function as catalysts for the formation of acid, are rendered non-hazardous by the ammonia under the distillation conditions.

The crude mixtures used for the fractional distillation, from which the excess alcohol was already advantageously removed in a first distillation, normally comprise 40 to 90 percent by weight of the monoalkylene glycol monoether, 10 to 50 percent by weight of the corresponding dialkylene glycol ether, and a residual amount of the higher alkylene glycol ethers. In addition to this, the mixtures still contain approximately 0.05 to 0.15 percent by weight of the basic catalyst such as NaOH or KOH. The success of the process according to this invention neither recognizably depends upon the type and amount of the basic catalyst used, nor on the product spectrum of the alkylene glycol ethers.

As is customary, the fractional distillation of the ether mixtures is carried out at 2 mbars to 1000 mbars absolute at a temperature of 50° C. to 200° C. either on a continuous basis or by batches so that more detailed information is not required. The ammonia is advantageously added to the feed of the distillation column.

Since the monoalkylene glycol ethers of methanol, ethanol, propanol, isopropanol, butanol, butan-3-ol, isobutanol, and tertiary butanol are of the greatest economic importance, the process according to this invention is applied particularly to these products. However, it is just as advantageous for the other products which correspond to formula I, that is, those which are derived from higher alkylene glycols (n=2 to 4).

EXAMPLE

A 100 kg of an ether mixture, which was obtained by reacting ethylene oxide with methanol (mole ratio 1:8.25) in the presence of 0.01 percent by weight of KOH as catalyst at a temperature of 170° C. and under 20 bars pressure and the subsequent separation of the excess methanol, were mixed with 0.06 grams (=0.6 ppm) of ammonia and were subsequently subjected to fractional distillation at temperatures of 92° C. to 170° C. and under 10 mbars to 250 mbars of pressure (absolute).

Obtained were 89 kg of ethylene glycol monomethyl ether as the main fraction (92° C., 250 mbars). A sample of this fraction taken immediately after the distillation was diluted with three times the amount of water. At room temperature this solution had a pH value of 6.8.

A corresponding sample taken after a storage period of two months had a pH value of 6.5.

If the fractional distillation was carried out under the same conditions but without the ammonia, the pH value of the aqueous sample solution dropped from an initial 6.8 to 4.0 after one week.

The same findings were obtained in the case of the ethylene glycol monoethyl ether.

The embodiments of the invention in which an exclusive privilege or property is claimed are defined as follows:

1. In a process for the preparation of storage-stable alkylene glycol monoalkyl ethers having the general formula $$R-(O-A-)_n OH \qquad (I)$$

in which A denotes an ethylene or propylene group, R represents a $C_1$ to $C_4$ alkyl group, and n has a value of 1 to 4, which involves the fractional distillation of a glycol ether mixture which is obtained by the alkali catalyzed reaction of ethylene oxide or propylene oxide with an alcohol, the improvement comprises carrying out the fractional distillation in the presence of 0.1 to 20 ppm of ammonia, relative to the amount of mixture used.

2. The process of claim 1 wherein A is ethylene.
3. The process of claim 1 wherein R is methyl.
4. The process of claim 1 wherein R is ethyl.
5. The process of claim 1 wherein n is 1.